United States Patent [19]
Portnoy

[11] Patent Number: 5,984,685
[45] Date of Patent: Nov. 16, 1999

[54] MEDICAL ACTION SYSTEM

[75] Inventor: Jay M. Portnoy, Overland Park, Kans.

[73] Assignee: The Children's Mercy Hospital, Kansas City, Mo.

[21] Appl. No.: 09/130,156

[22] Filed: Aug. 6, 1998

[51] Int. Cl.$^6$ .......................... G09B 23/28; A63B 23/00; B42D 15/00
[52] U.S. Cl. .......................... 434/262; 434/247; 283/900
[58] Field of Search .......................... 434/262, 267, 434/365, 219, 247; 283/900, 36, 67, 70, 74

[56] References Cited

U.S. PATENT DOCUMENTS

| | | |
|---|---|---|
| 1,526,717 | 2/1925 | Nunez . |
| 1,988,634 | 1/1935 | Stonecypher . |
| 2,248,162 | 7/1941 | Araujo . |
| 3,186,111 | 6/1965 | Lawlor . |
| 3,571,947 | 3/1971 | Maddison .............................. 434/262 |
| 3,979,839 | 9/1976 | Blanie . |
| 4,464,122 | 8/1984 | Fuller et al. . |
| 4,472,146 | 9/1984 | Weissbrod . |
| 4,865,549 | 9/1989 | Sonsteby . |
| 4,991,877 | 2/1991 | Lieberman . |
| 5,261,702 | 11/1993 | Mayfield . |
| 5,304,066 | 4/1994 | Sontag . |
| 5,312,257 | 5/1994 | Tarvin et al. . |
| 5,338,202 | 8/1994 | Saari . |
| 5,431,450 | 7/1995 | Coleman . |
| 5,498,034 | 3/1996 | Ford .......................... 253/67 |
| 5,580,254 | 12/1996 | Ramsey . |
| 5,632,510 | 5/1997 | Morowitz . |
| 5,702,253 | 12/1997 | Bryce et al. . |
| 5,720,502 | 2/1998 | Cain . |
| 5,727,949 | 3/1998 | Bar-Or et al. . |
| 5,743,407 | 4/1998 | Williams . |
| 5,746,603 | 5/1998 | Foster et al. .......................... 434/219 |
| 5,759,043 | 6/1998 | Craig . |
| 5,788,505 | 8/1998 | Sharkey .......................... 434/262 |

FOREIGN PATENT DOCUMENTS

| | | | |
|---|---|---|---|
| 1364088 | 5/1964 | France .......................... 434/262 |

*Primary Examiner*—Robert A. Hafer
*Assistant Examiner*—Michael B. Priddy
*Attorney, Agent, or Firm*—Hovey, Williams, Timmons & Collins

[57] ABSTRACT

A multiple-card, color-coded medical action system is provided to assist patients suffering from a chronic disease (e.g., asthma, sinusitis, or diabetes) which may exhibit symptoms of differing degrees of severity at different times. The system includes a plurality of interconnected cards imprinted with information about the chronic disease and treatments therefor; the cards include a number of symptom description/medical advice cards of different colors respectively, with the latter cards having imprinted thereon different symptom descriptions characteristic of different degrees of symptom severity, and corresponding medical information about the described symptoms.

9 Claims, 11 Drawing Sheets

MEDICAL ACTION SYSTEM

BACKGROUND OF THE INVENTION

1. Field of the Invention

The present invention is broadly concerned with medical action systems designed specifically for patients suffering from chronic diseases such as asthma, sinusitis and diabetes, in order to provide comprehensive symptom and medical advice information in a compact, easy-to-use format. More particularly the invention relates to such medical action systems made up of a plurality of interconnected, imprinted, color-coded cards which include symptom description/medical action cards of different colors respectively allowing the user to readily determine the severity of symptoms and recommended treatments.

2. Description of the Prior Art

Patients afflicted with chronic diseases commonly experience symptoms of varying severity. For example, asthma patients may have for extended periods only normal symptoms not requiring any special treatment steps. From time to time however, considerably more severe and even life-threatening symptoms can be present. It may be difficult in such cases for the patient to promptly recognize the problem and its potential severity, and to understand what types of treatment or care should be undertaken. This is particularly true in cases of children suffering from asthma, who may lack sufficient articulation to explain their symptoms. These problems of course exist in varying degrees with other chronic diseases.

The type of symptom-recognition and treatment information required for chronically ill patients does exist for most diseases. However, this information is widely dispersed in printed publications not realistically available to patients, or perhaps is comprehensively known only to medical professionals.

There is accordingly a real and unsatisfied need for a medical action system which provides symptom-recognition and treatment information for chronic diseases in a compact, easily usable format which can be understood and applied by patients.

SUMMARY OF THE INVENTION

The present invention overcomes the problems outlines above and provides a medical action system to assist patients suffering from a chronic disease which may exhibit symptoms of different severity at different times. Broadly speaking, the system of the invention comprises a plurality of interconnected indicia-bearing cards imprinted with information about the chronic disease and treatments therefor. The cards set includes a number of symptom description/medical advice cards of different cards respectively, wherein each of the differently colored symptom description/medical advice cards as imprinted thereon different symptom descriptions characteristic of a different degree of disease symptom severity, and corresponding medical information (usually including treatment information) about the described symptoms.

The colored cards making up the system of the invention are preferably of about the same size, and can be interconnected by binding along one margin or simple corner-bradding. To this end, the cards should have a maximum length or width dimension of up to about 8 inches; particularly preferred card sizes are of those of standard index cards, such as 4 inches×6 inches. In this way, the card pack can be carried in pocket or purse for easy reference.

In preferred forms, the symptom description/medical advice cards include a green colored card describing mild symptoms, a yellow card describing more severe symptoms, and a red card describing the most severe symptoms. All other cards of the pack have a color different from those used with the symptom description/medical advice cards, so that the latter may be readily recognized within the pack.

DETAILED DESCRIPTION OF THE PREFERRED EMBODIMENT

Figure 21:
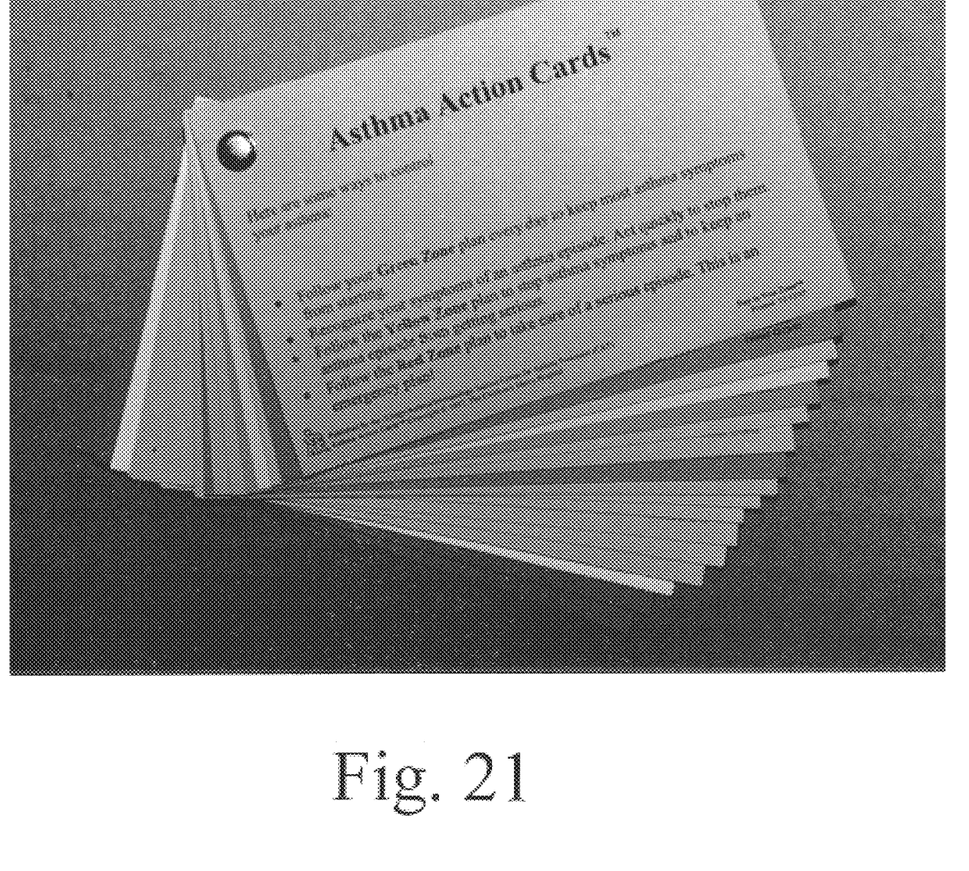
FIG. 21 is a photograph illustrating the multiple-card medical action system of the invention, with the differently colored cards thereof slightly separated to show the overall construction.

The medical action of the system invention is made up of a plurality of interconnected indicia-bearing cards which are designed to be portable and carried with a patient. A best seen in FIG. 21, the cards making up the overall system are each of approximately equal size (preferably about 4 inches×6 inches), and are interconnected at a common corner by any conventional means such as the depicted brad.

In detail, the medical action system for asthma is made up of a total of 19 preprinted paper stock cards. Cards 1–18 shown in corresponding FIGS. 1–18 are printed on one side only, whereas the last card 19 is printed on both sides (see FIGS. 19–20). Cards 1–17 contain patient information about asthma, whereas card 18 is designed to receive patient-supplied identifying and emergency information. Card 19 is an asthma classification card which is designed for use by medical professionals and is not intended to be given to a patient.

Figure 1:
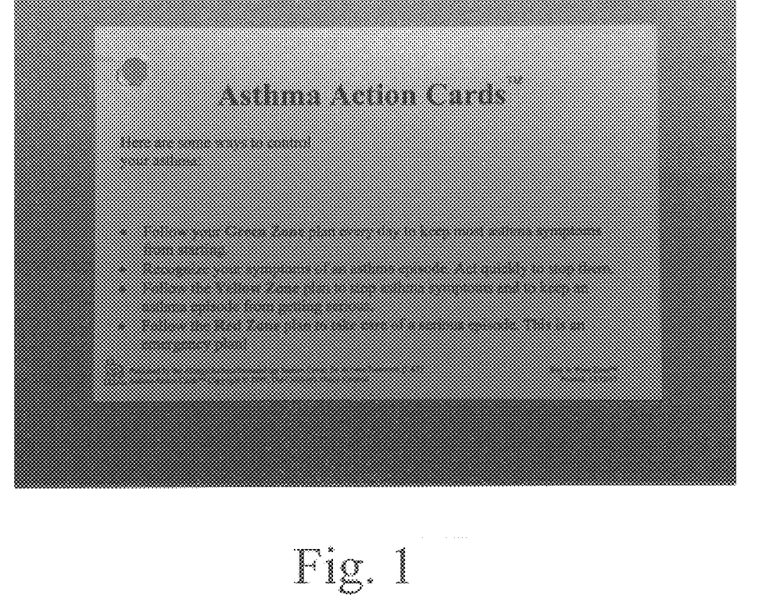
FIG. 1 is a photograph illustrating the first orange card in the medical action card system depicted in FIG. 21.
Figure 2:
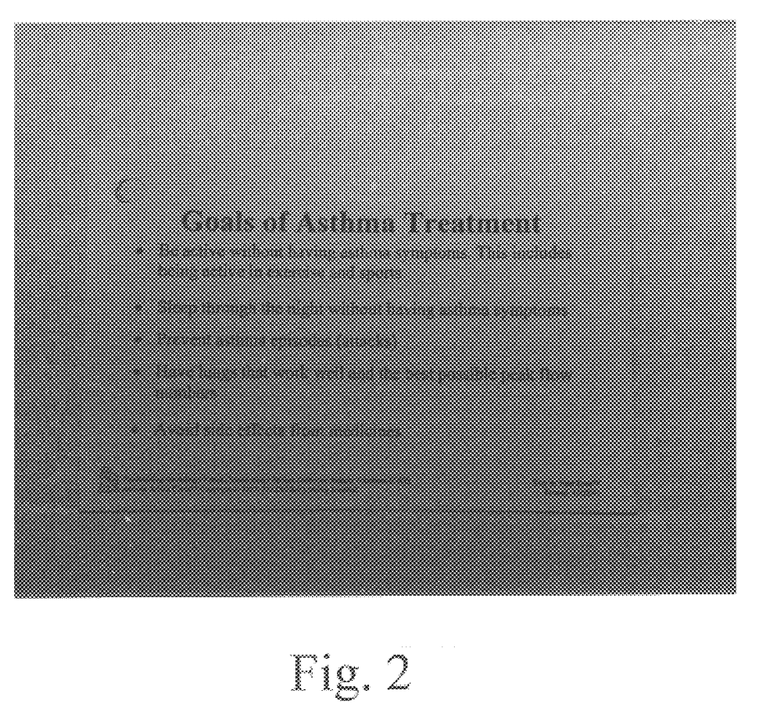
FIG. 2 is a photograph illustrating the second purple card in the medical action card system depicted in FIG. 21.

Card 1 (orange) is a front title card for the system and contains information explaining the use of the symptom description/medical advice cards (cards 3–5) within the card pack. Card 2 (purple) contains information about the overall goals of treatment for asthma.

Figure 3:
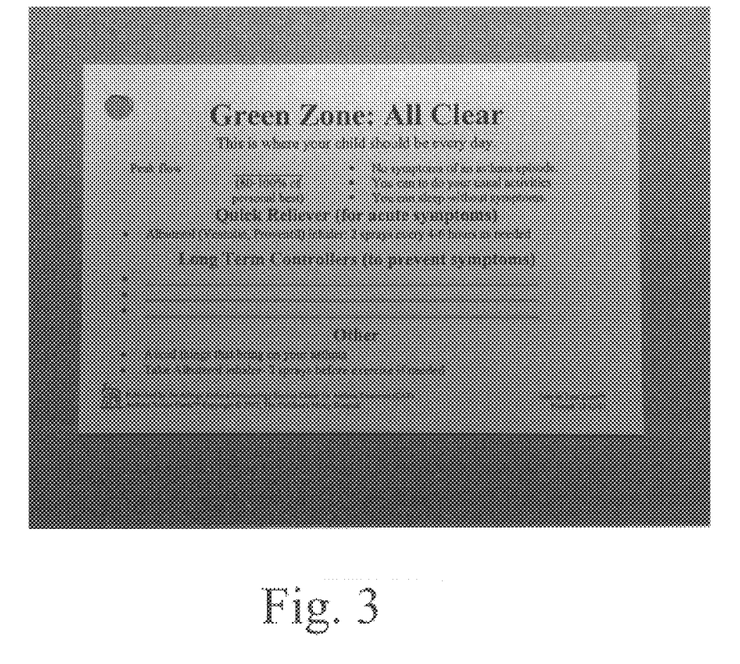
FIG. 3 is a photograph illustrating the third green card in the medical action card system depicted in FIG. 21, which is one of the symptom description/medical advice cards.
Figure 4:
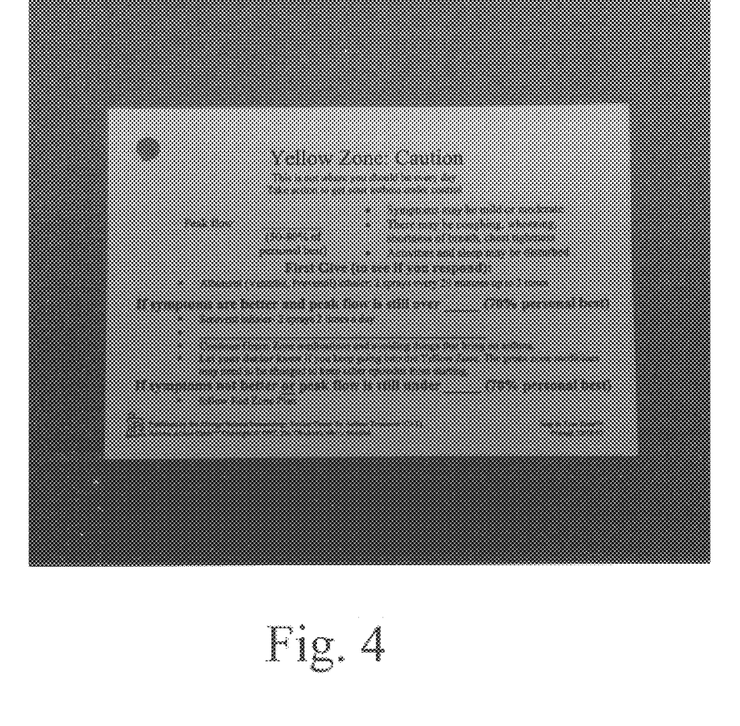
FIG. 4 is a photograph illustrating the forth yellow card in the medical action card system depicted in FIG. 21, which is one of the symptom description/medical advice cards.
Figure 5:
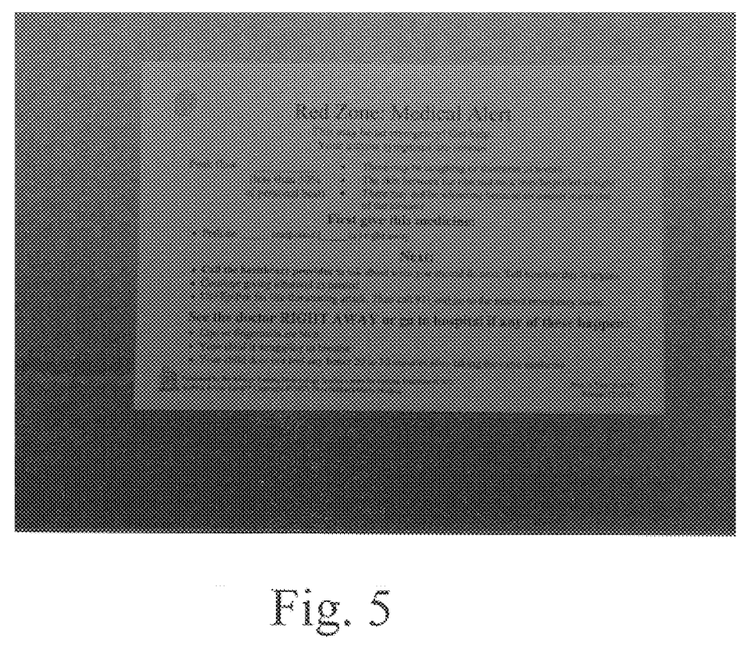
FIG. 5 is a photograph illustrating the fifth red card in the medical action card system depicted in FIG. 21, which is one of the symptom description/medical advice cards.
Figure 6:
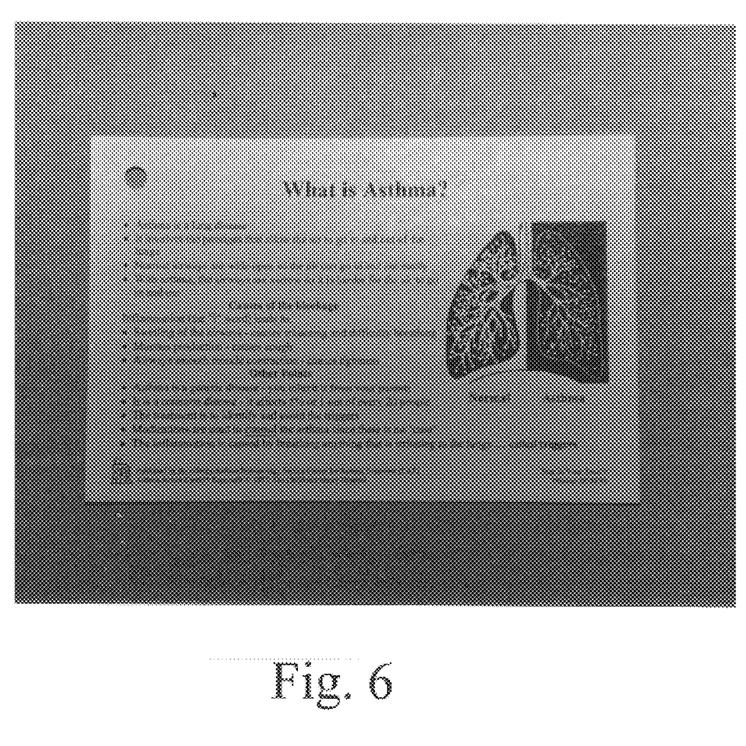
FIG. 6 is a photograph illustrating the sixth purple card in the medical action card system depicted in FIG. 21.
Figure 7:
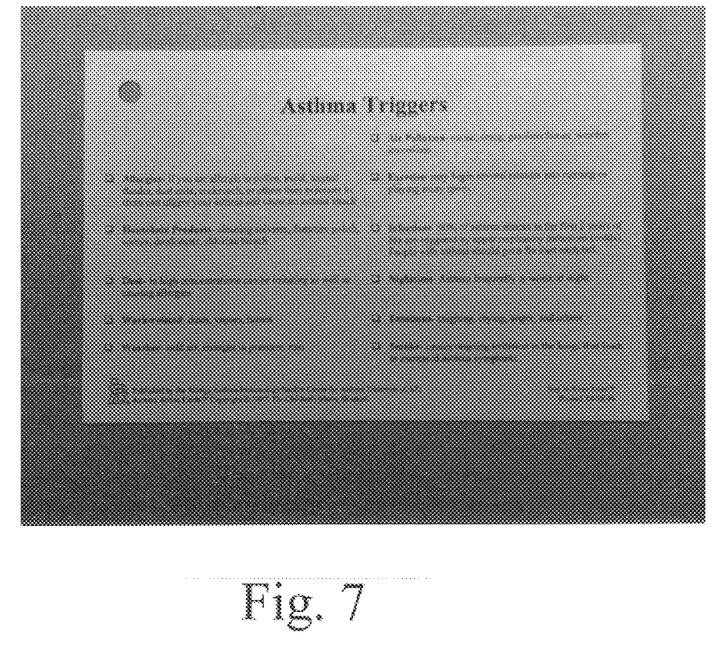
FIG. 7 is a photograph illustrating the seventh purple card in the medical action card system depicted in FIG. 21.
Figure 8:
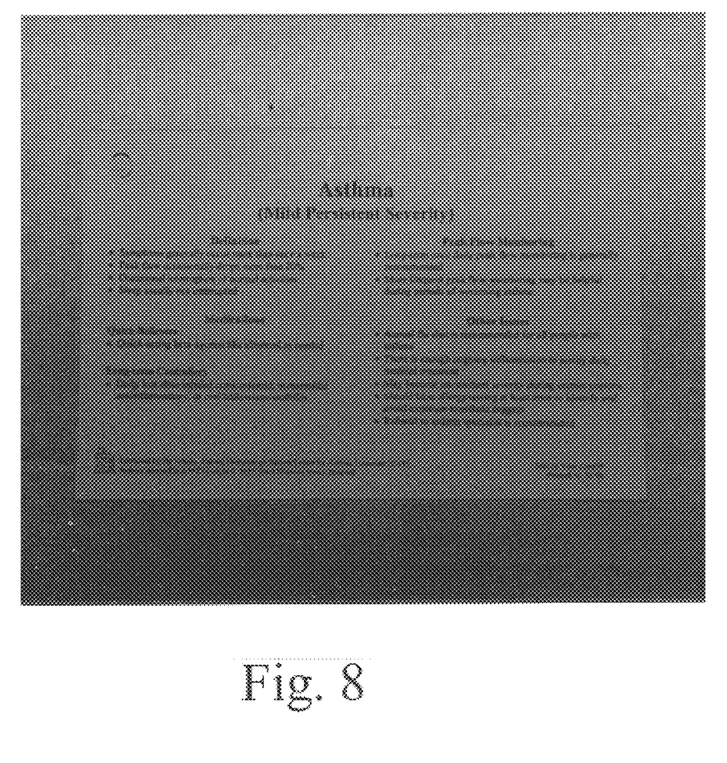
FIG. 8 is a photograph illustrating the eighth orange card in the medical action card system depicted in FIG. 21.
Figure 9:
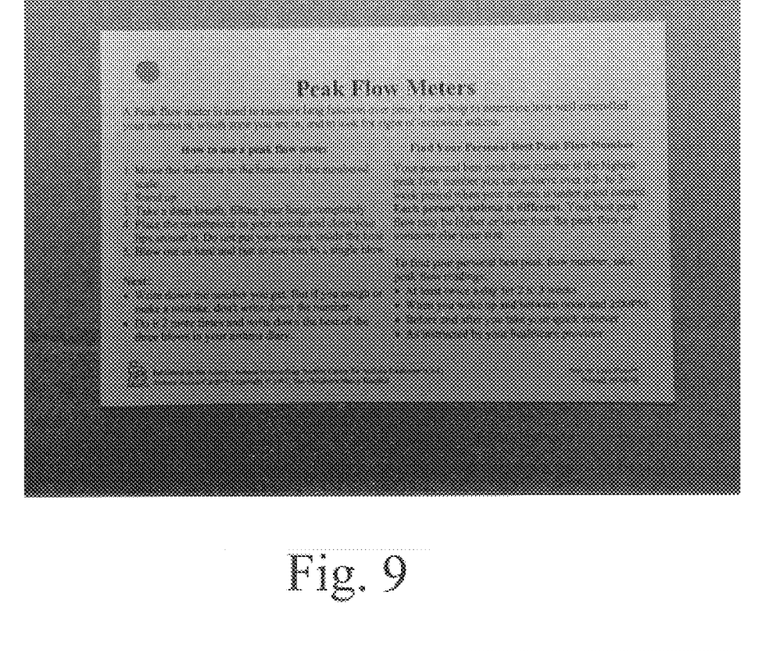
FIG. 9 is a photograph illustrating the ninth purple card in the medical action card system depicted in FIG. 21.
Figure 10:
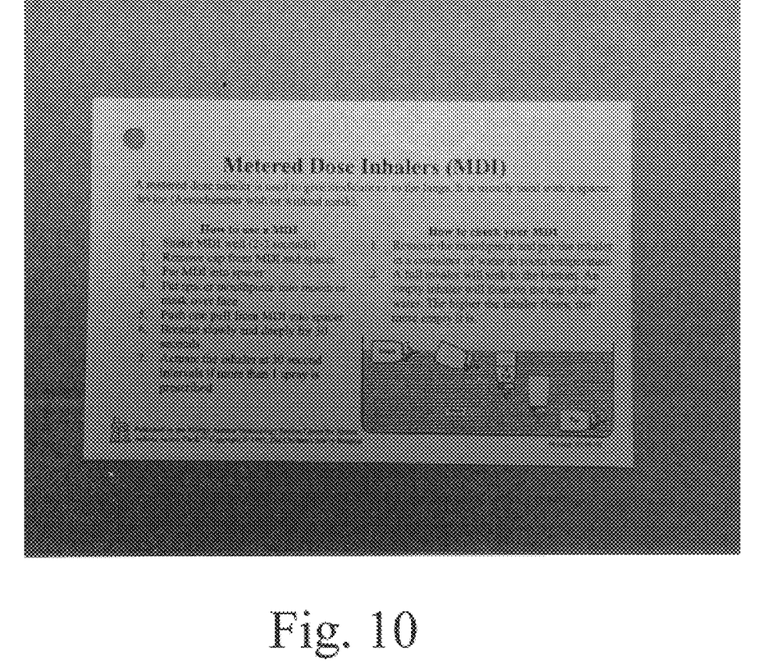
FIG. 10 is a photograph illustrating the tenth purple card in the medical action card system depicted in FIG. 21.
Figure 11:
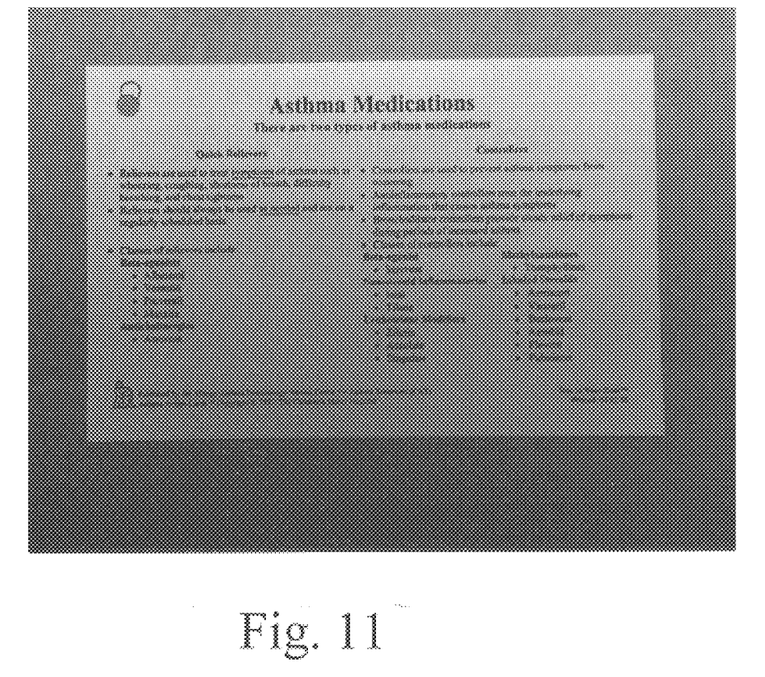
FIG. 11 is a photograph illustrating the eleventh blue card in the medical action card system depicted in FIG. 21.
Figure 12:
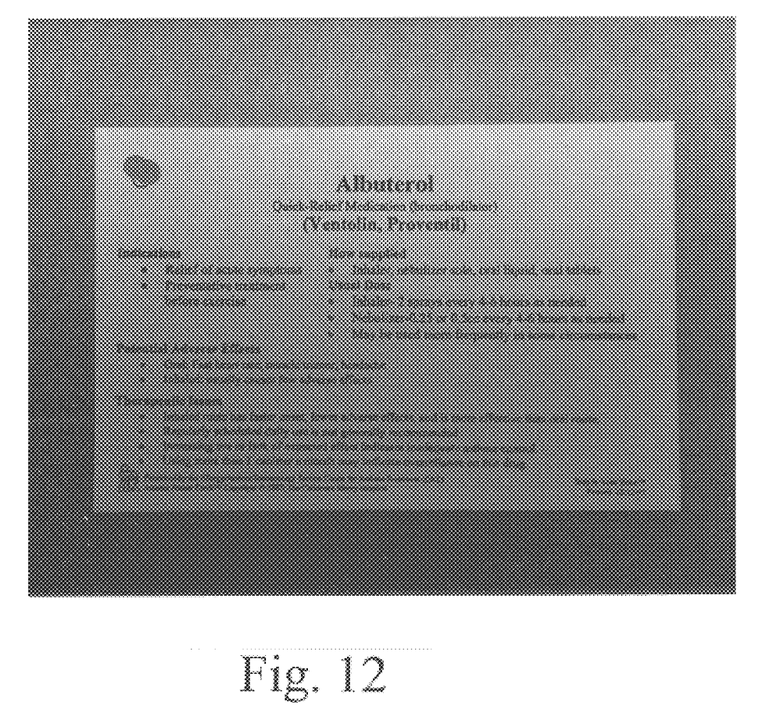
FIG. 12 is a photograph illustrating the twelfth blue card in the medical action card system depicted in FIG. 21.
Figure 13:
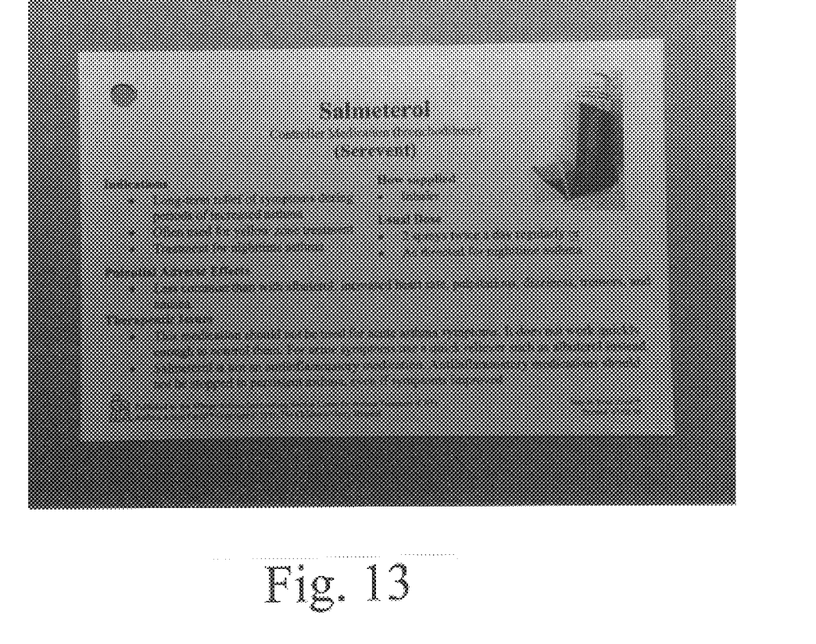
FIG. 13 is a photograph illustrating the thirteenth blue card in the medical action card system depicted in FIG. 21.
Figure 14:
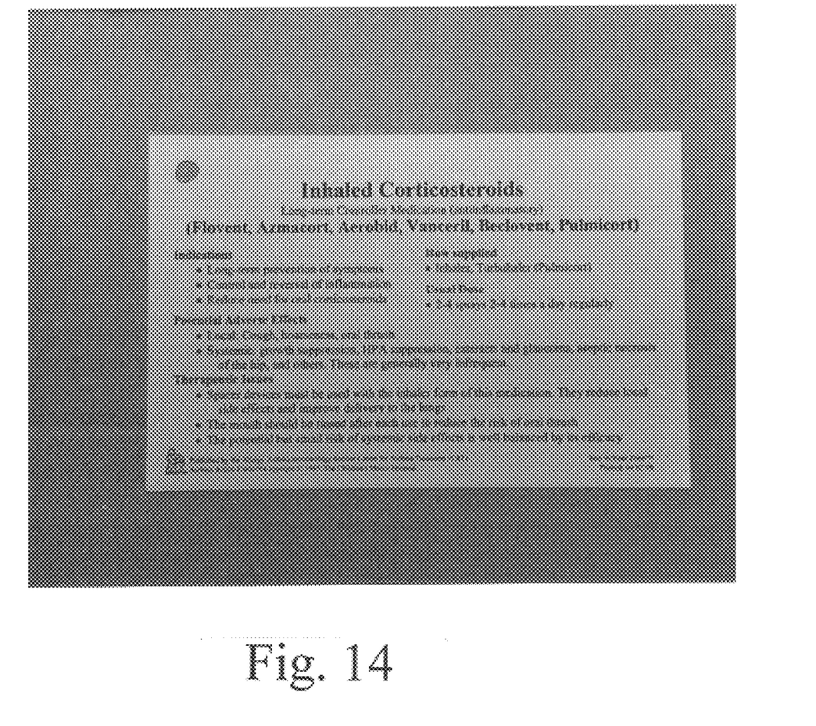
FIG. 14 is a photograph illustrating the fourteenth blue card in the medical action card system depicted in FIG. 21.
Figure 15:
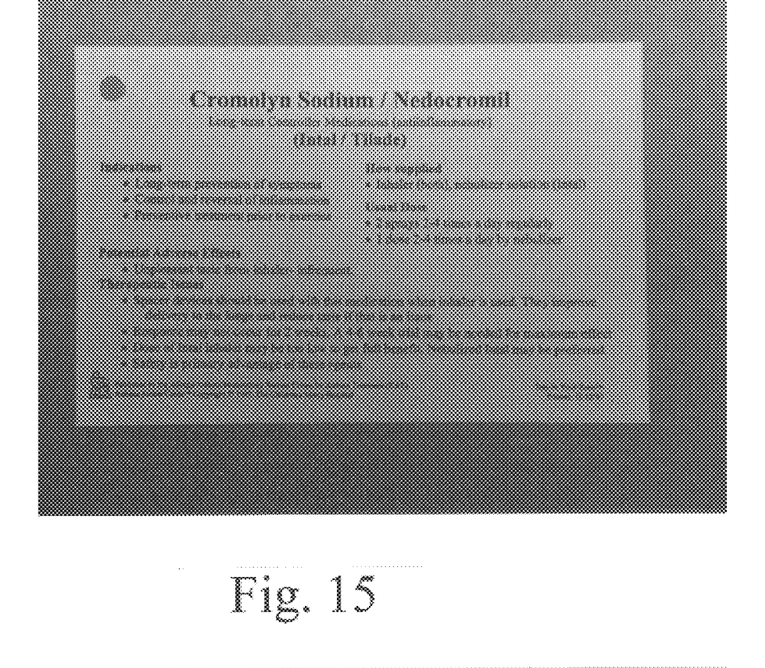
FIG. 15 is a photograph illustrating the fifteenth blue card in the medical action card system depicted in FIG. 21.
Figure 16:
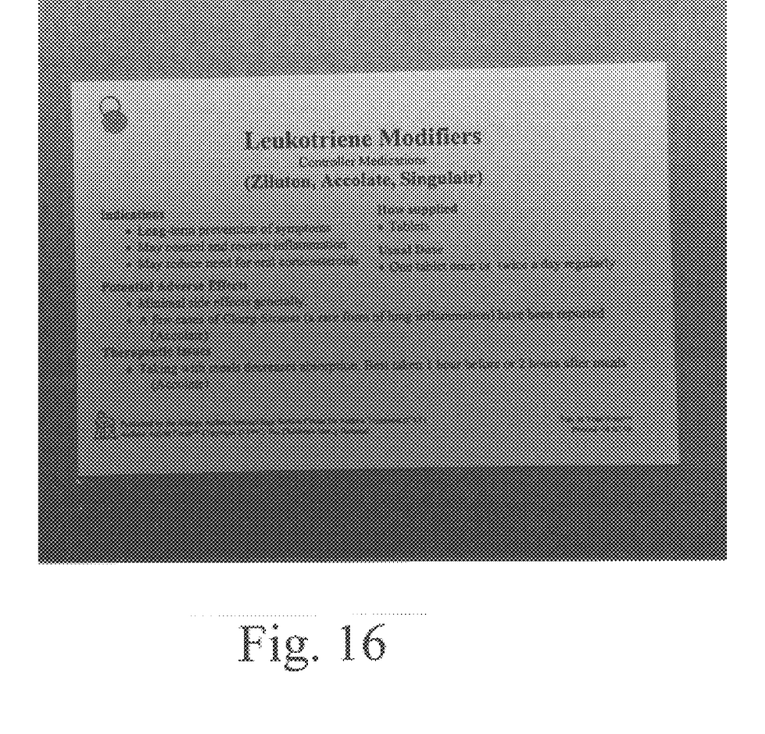
FIG. 16 is a photograph illustrating the sixteenth blue card in the medical action card system depicted in FIG. 21.
Figure 17:
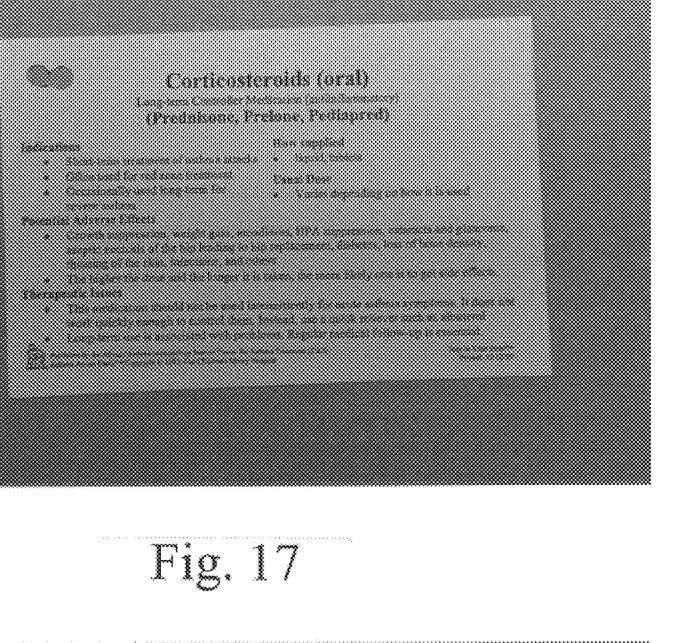
FIG. 17 is a photograph illustrating the seventeenth blue card in the medical action card system depicted in FIG. 21.

Cards 3–5 (respectively colored green, yellow and red) are symptom description/medical advice cards and include important imprinted information comprising symptom descriptions characteristic of differing degrees of asthma symptom severity, and corresponding medical information about the described symptoms. As illustrated in FIGS. 3–5, the green card describes the mildest asthma symptoms normally encountered and corresponding treatments; the yellow card describes more severe asthma symptoms and corresponding treatments; and the red card describes the most severe asthma symptoms and medical advice including treatment information. It will be appreciated that the use of green, yellow and red cards for the symptom description/medical advice cards can be varied, but this color scheme is preferred in that it mimics the traffic signal scheme of green-go, yellow-caution and red-stop.

Card 6 (purple) describes the nature of asthma and the etiology thereof. Card 7 (purple) describes typical triggers for asthma. Card 8 (orange) describes mild persistent symptoms of asthma as well as medications, monitoring techniques, and other related issues. Card 9 (purple) describes a monitoring technique for asthma, in this case use of a peak flow meter for asthma monitoring.

Card 10 (purple) describes the nature and use of metered dose inhalers in asthma treatment. Card 11 (blue) describes various classes of asthma medications. Cards 12–17 (all blue) describe specific asthma medications with indications, adverse effects, therapeutic issues, administration modalities, and normal dosages.

Figure 18:
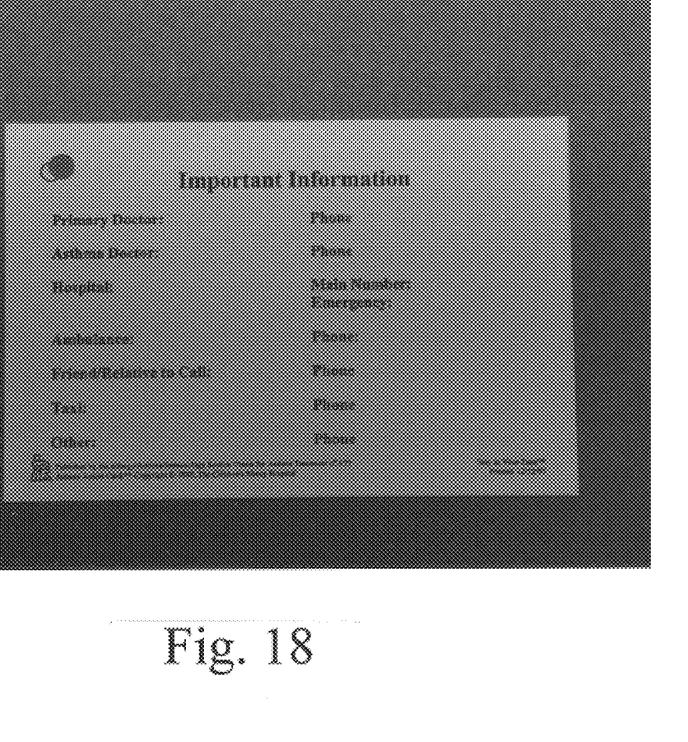
FIG. 18 is a photograph illustrating the eighteenth white card in the medical action card system depicted in FIG. 21.
Figure 19:
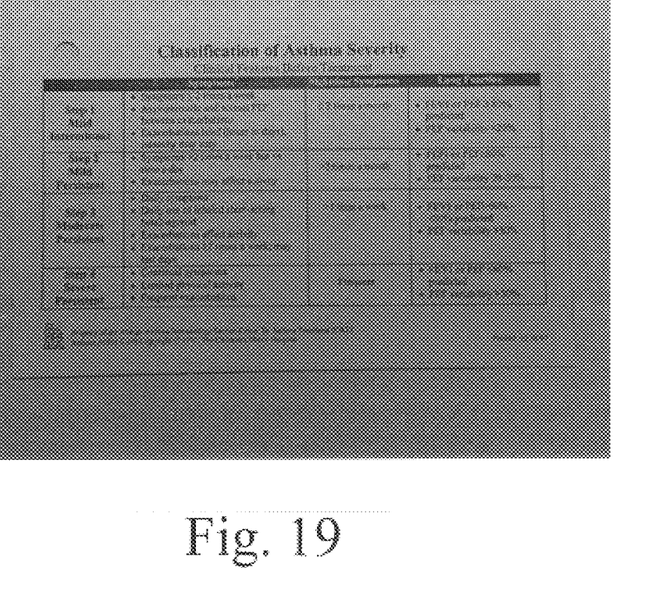
FIG. 19 is a photograph illustrating the front of the nineteenth purple card in the medical action card system depicted in FIG. 21.
Figure 20:
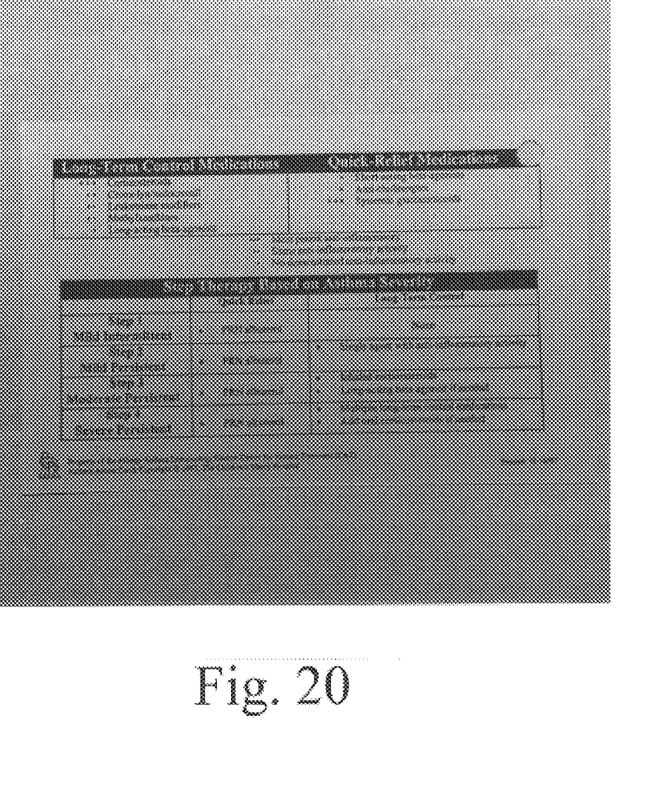
FIG. 20 is a photograph illustrating the back of the nineteenth purple card in the medical action card system depicted in FIG. 21.

Card 18 (white) is a card to receive patient information related to the disease. Card 19 (purple) is designed for medical professional and includes a classification of symptoms, corresponding lung functions, long-term and quick-relief medications and step therapy based on asthma severity.

The multiple-card pack is designed to be carried by the patient and provides ready reference for different levels of asthma symptoms. Thus, the user my readily refer to the green/yellow/red symptom description/medical advice cards to quickly determine the severity of symptoms and corresponding medical advice. The remainder of the cards provide useful information for the asthma sufferer. To give but one example, if the symptoms described in red card five (lips or fingernails blue, struggling to breath and lack of response to medication) are evident, the card indicates a medical alert and directs the patient to a hospital for emergency care.

It will also be understood that other specific medical action system card packs may be prepared for other diseases such as sinusitis which are both chronic and characterized by symptoms of varying severity and the need for different treatments in response to such different symptoms.

I claim:

1. A medical action system to assist patients suffering from a chronic disease which may exhibit symptoms of differing degrees of severity at different times, said system comprising a plurality of interconnected indicia-bearing cards imprinted with information about a single and disease and treatments therefor, said plurality of cards including a number of symptom description/medical advice cards, each of said symptom description/medical advice cards being of a different predominant color respectively, with each of the differently colored symptom descriptionnnical advice cards having imprinted thereon different symptom descriptions characteristic of a different degree of severity of symptoms of said and upifir disease, and corresponding medical information about the described symptoms whereby a patient suffering from a certain degree of deverity of symptoms of said single and specific disease can refer to said cards and quickly find a card corresponding to the certain degree of severity of symptoms.

2. The system of claim 1, said cards being of substantially the same size.

3. The system of claim 1, said cards having a maximum length or width dimension of up to about 8 inches.

4. The system of claim 1, said cards being interconnected at a common corner thereof.

5. The system of claim 1, said symptom description/medical advice cards including a green colored card describing mild symptoms of said disease, a yellow colored card describing more severe symptoms of said disease, and a red colored card describing the most severe symptoms of said disease.

6. They system of claim 1, said disease being selected from the group consisting of asthma, sinusitis and diabetes.

7. The system of claim 1, said cards also including a card imprinted with information about the goals of treatment of the disease, a card imprinted with information about the nature of the disease, and a card imprinted with medicament information.

8. The system of claim 1, said cards having a width of about 4 inches and a length of about 6 inches.

9. The system of claim 1, said medical information including treatment information corresponding to said described symptoms.

* * * * *